US006835865B2

(12) United States Patent
Quincy, III

(10) Patent No.: US 6,835,865 B2
(45) Date of Patent: Dec. 28, 2004

(54) ANTIMICROBIAL NONWOVEN WEBS FOR PERSONAL CARE ABSORBENT ARTICLES

(75) Inventor: Roger Bradshaw Quincy, III, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 120 days.

(21) Appl. No.: 10/037,466

(22) Filed: Dec. 21, 2001

(65) Prior Publication Data

US 2003/0144638 A1 Jul. 31, 2003

(51) Int. Cl.$^7$ ................................. A61F 13/15
(52) U.S. Cl. ....................... 604/359; 604/360
(58) Field of Search ................. 604/359, 360

(56) References Cited

U.S. PATENT DOCUMENTS

| 3,338,992 | A | | 8/1967 | Kinney | |
|---|---|---|---|---|---|
| 3,341,394 | A | | 9/1967 | Kinney | |
| 3,502,538 | A | | 3/1970 | Petersen | |
| 3,502,763 | A | | 3/1970 | Hartmann | |
| 3,542,615 | A | | 11/1970 | Dobo et al. | |
| 3,692,618 | A | | 9/1972 | Dorschner et al. | |
| 3,802,817 | A | | 4/1974 | Matsuki et al. | |
| 3,849,241 | A | | 11/1974 | Butin et al. | |
| 4,340,563 | A | | 7/1982 | Appel et al. | |
| 4,663,220 | A | | 5/1987 | Wisneski et al. | ........... 428/221 |
| 4,842,593 | A | * | 6/1989 | Jordan et al. | ........... 604/360 |
| 4,940,464 | A | | 7/1990 | Van Gompel et al. | ........ 604/396 |
| 5,046,272 | A | | 9/1991 | Vogt et al. | ............. 38/143 |
| 5,104,116 | A | | 4/1992 | Pohjola | ............. 271/185 |
| 5,224,405 | A | | 7/1993 | Pohjola | ............... 83/24 |
| 5,226,992 | A | | 7/1993 | Morman | ............ 156/62.4 |
| 5,490,983 | A | | 2/1996 | Worley et al. | ........... 424/405 |
| 5,882,357 | A | | 3/1999 | Sun et al. | ............... 8/189 |
| 6,020,491 | A | * | 2/2000 | Wonley et al. | ........... 544/220 |
| 6,183,763 | B1 | * | 2/2001 | Beerse et al. | ........... 424/404 |
| 6,548,054 | B2 | * | 4/2003 | Worley et al. | ........... 424/78.36 |
| 2002/0077612 | A1 | * | 6/2002 | Quincy | ............ 604/358 |
| 2003/0044377 | A1 | * | 3/2003 | Worely et al. | ........... 424/78.22 |

FOREIGN PATENT DOCUMENTS

| EP | 0 217 032 | 4/1987 | ......... D04H/13/00 |
|---|---|---|---|
| WO | WO 98/10648 | 3/1998 | ......... A01N/33/00 |
| WO | WO 00/29101 | 5/2000 | ......... B01D/69/02 |
| WO | WO 02/30477 A1 | 4/2002 | ......... A61L/9/00 |

* cited by examiner

Primary Examiner—John J. Calvert
Assistant Examiner—C. Lynne Anderson
(74) Attorney, Agent, or Firm—Pauley Petersen & Erickson

(57) ABSTRACT

Antimicrobial nonwoven webs are provided which have odor control properties in addition to antibacterial properties, and which can be used in personal care absorbent articles. The nonwoven webs are treated with a stable halogenated polystyrene hydantoin which does not release halogen during storage or use of the absorbent article. The halogen atoms are attached to the amide nitrogen atoms in the polystyrene hydantoin, and are not attached to the imide nitrogen atoms.

34 Claims, No Drawings

ANTIMICROBIAL NONWOVEN WEBS FOR PERSONAL CARE ABSORBENT ARTICLES

FIELD OF THE INVENTION

This invention relates to an antimicrobial nonwoven web for personal care absorbent articles, which provides both antimicrobial and odor control properties.

BACKGROUND OF THE INVENTION

Nonwoven webs used in personal care absorbent articles can harbor bacteria, particularly when in contact with bodily fluids. Some of this bacteria can cause, or help cause skin rash and other discomfort to the wearer of the absorbent article. Some of this bacteria causes odor. It is known to use antimicrobial agents to reduce or prevent bacteria growth. However, antimicrobial agents themselves may contribute to skin rash and other discomfort. Therefore, it is usually not desirable to use an antimicrobial agent which affects the bacteria typically found at or near the surface of the wearer's skin.

There is a need or desire for antimicrobial nonwoven webs useful in absorbent articles which can prevent or inhibit growth of bacteria, including bacteria found at or near the wearer's skin, without promoting skin irritation or other discomfort.

SUMMARY OF THE INVENTION

The present invention is directed to an antimicrobial nonwoven web useful in personal care absorbent articles. The antimicrobial nonwoven web contains an antimicrobial agent which reduces or prevents bacteria growth without causing harm or discomfort to the wearer's skin. The antimicrobial agent is a stable halogenated polystyrene hydantoin which does not release the halogen (e.g., chlorine) over time. Polystyrene hydantoin generally contains both an amide nitrogen and an imide nitrogen which can be chemically linked to a halogen (e.g., chlorine or bromine). The inventor has discovered that nonwoven webs treated with chlorinated polystyrene hydantoin are stable, and do not release chlorine, when chlorine atoms are linked entirely to the amide nitrogen sites in the polystyrene hydantoin molecules, and are not linked to the imide nitrogen sites.

The nonwoven web treated with the stable halogenated polystyrene hydantoin can be any of the nonwoven webs used in an absorbent article which are exposed to an aqueous liquid insult. For instance, the nonwoven web may be a cellulose nonwoven web, such as is used in an absorbent core. The nonwoven web may also be a spunbond web, a melt blown web, a bonded carded web, an air laid web, or the like, such as are used in a bodyside liner and/or surge layer of a personal care absorbent article.

DEFINITIONS

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. The term also includes cellulose fiber webs and other absorbent fiber webs formed using various processes, as well as apertured films having openings for passing liquid. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "cellulose fibers" refers to fibers from wood, paper, woody plants, and certain non-woody plants. Woody plants include, for example, deciduous and coniferous trees. Non-woody plants include, for instance, cotton, flax esparto grass, milkweed, straw, jute hemp, and bagasse.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average diameters larger than about 7 microns, more particularly, between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface.

The term "microfibers" means small diameter fibers having an average diameter not greater than about 75 microns, for example, having an average diameter of from about 1 micron to about 50 microns, or more particularly, microfibers may have an average diameter of from about 1 micron to about 30 microns. Another frequently used expression of fiber diameter is denier, which is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9.

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "absorbent fibers" refers to fibers capable of absorbing about 5 to less than 15 times their weight in an aqueous solution containing 0.9 weight percent sodium chloride. The term is intended to include cellulose fibers, but not superabsorbent materials. "Nonabsorbent" or "non-retentive" fibers are fibers which absorb and retain less than about 5 times their weight in an aqueous solution containing 0.9% by weight sodium chloride.

"Superabsorbent" or "superabsorbent material" refers to a water-swellable, water-insoluble organic or inorganic material capable, under the most favorable conditions, of absorbing at least about 15 times its weight and, more desirably, at least about 20 times its weight of an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

The term "personal care absorbent article" includes without limitation diapers, training pants, swim wear, absorbent underpants, baby wipes, adult incontinence products, and feminine hygiene products.

The term "medical absorbent article" includes without limitation garments, underpads, bandages, absorbent drapes, and medical wipes.

DETAILED DESCRIPTION OF THE PRESENTLY PREFERRED EMBODIMENTS

In accordance with the invention, a nonwoven web having antimicrobial properties is provided. The nonwoven web contains a stable halogenated (desirably, chlorinated) polystyrene hydantoin, which does not release chlorine over time during storage and wear. The stable halogenated polystyrene hydantoin contains a repeating unit having the following chemical formula:

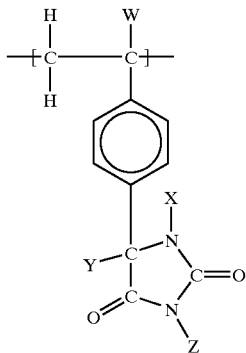

where
W=H or $CH_3$
X=Cl or Br
Y=any $C_1$–$C_4$ alkyl group
Z=H or any $C_1$–$C_4$ alkyl group For purposes of the invention, the positioning of the halogen group only on the amide nitrogen, as shown above, is important. If any of the repeating units has a) halogen atoms which are positioned only on the imide nitrogen, or b) halogen atoms positioned on both the amide nitrogen and the imide nitrogen, the polymer is less stable and halogen gas may be released. For this reason, at least about 90% of the total halogen atoms in the halogenated polystyrene hydantoin will be chemically linked to the amide nitrogens in the polymer. Suitably, at least about 95% and, desirably, at least about 99% of the total halogen atoms in the polymer will be chemically linked to the amide nitrogens in the polymer. Preferably, about 100% of the total halogen atoms will be chemically linked to the amide nitrogens in the polymer.

Another variable is the percentage of total amide nitrogens on the polystyrene hydantoin which are halogenated. The more amide sites which are halogenated, the better the antimicrobial and odor control properties will be. The percentage of amide nitrogens which are halogenated may range from about 10–100%, suitably about 50–100%, desirably about 75–100%.

The stable halogenated polystyrene hydantoin may alternatively employ either chlorine or bromine as the halogen. When bromine is used, the desired percentages and ranges may be the same as for chlorine. However, chlorine is the most desired halogen due to its combined antimicrobial and odor control properties. Iodine is less desirable because it contributes its own undesirable odor. Fluorine is less desirable because any amount of free fluorine may cause rashes and irritation to the wearer's skin to an even greater extent than free chlorine.

The stable halogenated polystyrene hydantoin is generally in the form of fine polymer particles which are added to and dispersed within the nonwoven web using conventional techniques. Alternatively, the halogenated polystyrene hydantoin may be melted and coated onto the nonwoven web using an extrusion process. Alternatively, the halogenated polystyrene hydantoin may be dissolved in a solvent and solution coated onto the nonwoven web using conventional techniques. A stable chlorinated polystyrene hydantoin which is useful in practicing the invention (i.e., in which all of the chlorine atoms are linked to amide nitrogens) has been produced by HaloSource Corporation in Seattle, Wash., and is designated Poly-1-Cl, Type 2. HaloSource Corporation also produced a previous chlorinated polystyrene hydantoin in which chlorine linkages were present on both the imide and amide nitrogen sites, designated as Poly-1-Cl, Type 1. Various N-halamine compounds are described in U.S. Pat. No. 6,162,452, which is incorporated by reference.

In one embodiment of the invention, the stable halogenated polystyrene hydantoin is added to an absorbent nonwoven web, such as a fibrous web used in an absorbent core of a personal care absorbent article or a medical absorbent article. Absorbent nonwoven webs used in absorbent cores can be manufactured in a wide variety of sizes and shapes, and from a wide variety of liquid absorbent materials commonly used in the art. For example, an absorbent nonwoven web can suitably include a matrix of hydrophilic fibers, such as a web of cellulosic fluff, mixed with particles of a high-absorbency material commonly known as superabsorbent material. In a particular embodiment, the absorbent nonwoven web includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent nonwoven web to better contain and absorb body exudates. The concentration of the superabsorbent particles can also vary through the thickness of the absorbent nonwoven web. Alternatively, the absorbent nonwoven web can include a laminate of fibrous webs and superabsorbent material or other suitable means of maintaining a superabsorbent material in a localized area. Another type of absorbent material suitable for the absorbent nonwoven web is coform, which can be a blend of cellulose fibers and melt-blown fibers. The weight ratio of cellulose fibers to melt-blown fibers may range between 30 (cellulose)/70 (melt-blown) and 90 (cellulose)/10 (melt-blown). Wood pulp fibers are preferred for the cellulose fibers and polypropylene is preferred for the melt-blown fibers. Superabsorbent materials may be added to the coform to increase fluid absorption capacity.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 20 times its weight in water.

In one embodiment, the absorbent nonwoven web is in the form of a generally rectangular absorbent core, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent nonwoven web in an amount of from about 0 to about 90 weight percent based on total weight of the absorbent core. The absorbent nonwoven web suitably has a density within the range of about 0.10 to about 0.35 grams per cubic centimeter. The absorbent core may or may not be wrapped or encompassed by a suitable tissue wrap that maintains the integrity and/or shape of the absorbent nonwoven web.

In another embodiment, an absorbent web useful as a food wipe or industrial wipe may contain a hydraulically entangled mixture of cellulose (desirably, wood pulp) fibers and thermoplastic (desirably, polypropylene) spunbond fibers. The hydraulically entangled mixture may contain about 5–95% by weight cellulose fibers and about 5–95% by weight spunbond fibers, suitably 50–95% by weight cellulose fibers and 5–50% by weight spunbond fibers, desirably 80–90% by weight cellulose fibers and 10–20% by weight spunbond fibers.

When the nonwoven web is an absorbent material, the amount of stable chlorinated polystyrene hydantoin added to the nonwoven web should be sufficient to combat the bacteria and odor formation that would otherwise be promoted by the amount of aqueous body liquid (e.g., urine) that the nonwoven web is designed to contain. Generally, the antimicrobial absorbent nonwoven web should contain about 0.1–10% by weight of the stable halogenated polystyrene hydantoin, suitably about 0.5–5% by weight, desirably about 1–3% by weight.

The nonwoven web may also be a thermoplastic nonwoven web useful in a bodyside liner of an absorbent article, or in a surge layer that may be positioned between the bodyside liner and the absorbent core. These nonwoven webs are often intended to transmit liquid quickly, and generally do not retain or absorb significant quantities of aqueous liquid. Nonwoven webs which transmit liquid include thermoplastic spunbond webs, meltblown webs, bonded carded webs, air laid webs and the like, made using conventional techniques. A wide variety of thermoplastic materials may be used to construct these non-retentive nonwoven webs, including without limitation polyamides, polyesters, polyolefins, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing. Polyolefins are desirable. Polyethylene and polypropylene homopolymers and copolymers are most desirable.

When the antimicrobial nonwoven web is used to transmit liquid materials instead of retaining them, a similar quantity of stable halogenated polystyrene hydantoin should be adequate to prevent bacteria growth and odors in that layer. Generally, the antimicrobial liquid-transmissive non-retentive nonwoven web should contain about 0.1–10% by weight of the stable halogenated polystyrene hydantoin, suitably about 0.5–5% by weight, desirably about 1–3% by weight.

The antimicrobial nonwoven web may be used in a wide variety of personal care absorbent articles. A personal care absorbent article commonly includes a liquid-transmissive bodyside liner, a liquid-transmissive surge layer below the bodyside liner, a liquid-absorbent core below the surge layer, and a moisture vapor permeable, liquid impermeable outer cover below the absorbent core. As explained above, the antimicrobial nonwoven web of the invention may be employed as any one or more of the liquid transmissive (non-retentive) and absorbent layers. Desirably, the antimicrobial nonwoven web is an absorbent nonwoven web useful in the absorbent core, because most of the bacteria and odor-generating liquid is stored in the absorbent core. Suitable personal care absorbent articles include diapers, training pants, swim wear, absorbent underpants, baby wipes, adult incontinence products, and feminine hygiene products.

The antimicrobial nonwoven web may also be used in a wide variety of medical absorbent articles. Medical absorbent articles include certain medical garments, underpads, bandages, drapes, and medical wipes. The antimicrobial web may also be used in other absorbent articles including industrial wipes, food wipes, and the like.

EXAMPLES

Headspace Chlorine Results for Poly-1-Cl

Drager tubes CH 24301 (Chlorine 0.2/a) with a standard measuring range of 0.2 to 3 ppm were used to determine headspace chlorine levels for various Poly-1-Cl samples. In the presence of chlorine gas ($Cl_2$), the tube will undergo a color change from white to yellow-orange. Bromine, chlorine dioxide, and nitrogen dioxide will also cause this color change. For an actual chlorine concentration of 0.2 to 3 ppm to be read from the tube, the requirement is for 10 strokes to be pulled through the tube using a Drager bellows type pump. Each stroke supplies 100 $cm^3$. If only one stroke or 100 $cm^3$ is pulled through the tube, then the measuring range for the tube will be 2 to 30 ppm. Drager tubes are available from SKC, Inc. located in Eighty-Four, Pa.

For the various Poly-1-Cl samples obtained from Halo-Source Corporation, Poly-1-Cl powder alone and in combination with saline was placed in a 20-cm³ headspace vial. The vial was crimped shut and left at ambient temperature for a desired length of time. Then, the vial was either tested for headspace chlorine or first placed in a GC oven at elevated temperature for a desired length of time before being tested. The headspace from the vial was tested for chlorine by piercing the septum of the vial cap with a needle that was attached to the Drager tube with rubber tubing. The headspace was removed with a 60-cm³ syringe that was attached to the other end of the Drager tube with rubber tubing. The septum of the vial cap was also pierced with a second needle in order for ambient air to replace the removed headspace air above the sample. The amount of headspace chlorine for a sample was calculated from the Drager tube reading, the number of 60-cm³ volumes removed, and the relationship that 1000 cm³ (10 strokes) must be pulled through the tube in order to read chlorine in a range of 0.2 to 3 ppm.

In the following Table 1, "Poly-1-Cl, Type 1" refers to chlorinated polystyrene hydantoin obtained from Halo-Source Corporation, in which both the amide and imide nitrogens are chlorinated "Poly-1-Cl, Type 2 " refers to chlorinated polystyrene hydantoin obtained from Halo-Source Corporation, in which only the amide nitrogen is chlorinated. As shown in Table 1, the chlorinated polystyrene hydantoin according to the invention, in which only the amide nitrogens were chlorinated, released less than 0.9 ppm of chlorine under a wide variety of different conditions. The chlorinated polystyrene hydantoin control, in which both the amide and imide nitrogens were chlorinated, released 68 ppm of chlorine over time at room temperature. This data illustrates that the selectively chlorinated polystyrene hydantoin of the invention is far more stable.

TABLE 1

Chlorine Release Over Time
The following table shows the headspace chlorine data for various Poly-1-Cl samples

| Example | Sample | Details | Tube Reading | Calculated Amount | Calculated per Piece[1] |
|---|---|---|---|---|---|
| 1 | Poly-1-Cl Type-1, Dry | 12 days at room temp. | >3 ppm | >50 ppm | >68 ppm |
| 2 | Poly-1-Cl Type-2, Dry | 6 days at room temp. | <<<0.2 ppm | <<<0.7 ppm | <<<0.9 ppm |
| 3 | Poly-1-Cl Type-2, Wet | +300% saline[3], 6 days at room temp. | <0.2 ppm[2] | <0.7 ppm[2] | <0.9 ppm[2] |
| 4 | Poly-1-Cl Type-2, Dry, Elevated Temp. | 1 day at room temp., 20 min at 50° C. | <<0.2 ppm | <<0.7 ppm | <<0.9 ppm |
| 5 | Poly-1-Cl Type-2, Wet, Elevated Temp. | +300% saline, 1 day at room temp., 30 min at 37° C. | <<<0.2 ppm | <<<0.7 ppm | <<<0.9 ppm |
| 6 | Poly-1-Cl Type-2, Wet, Elevated Temp. | +300% saline, 1 day at room temp., 20 min at 50 ° C. | <<<0.2 ppm | <<<0.7 ppm | <<<0.9 ppm |
| 7 | Poly-1-Cl Type-2, Wet, Elevated Temp. | +300% saline, 18.5 hours at 40° C. | <0.2 ppm | <0.7 ppm | <0.9 ppm |
| 8 | Poly-1-Cl Type-2, Wet, Elevated Temp. | +300% saline, 24.5 hours at 40° C. | <0.2 ppm | <0.7 ppm | <0.9 ppm |

[1]"Calculated per Piece" was determined by taking the "Calculated Amount of chlorine, dividing by the weight of Poly-1-Cl in the headspace tube (ca. 0.05 g), and then multiplying by the amount of Poly-1-Cl in a 3-inch diameter piece of 600 gsm fluff that contains 2.5 wt % Poly-1-Cl (0.0684 g).
[2]These values were determined from a Drager tube that had been previously used for the "Poly-1-Cl Type-2, Dry" sample. Therefore, the reported values are probably higher than values that would have occurred with a new tube. New tubes were used for all other samples.
[3]The saline solution was 0.9% NaCl in water. The term "+300% saline" refers to 3 parts saline solution per one part Poly-l-Cl.

Antimicrobial Test Results

Samples of selectively chlorinated polystyrene hydantoin (Poly-1-Cl, Type 2, chlorinated only on the amide nitrogens) were blended at 1% by weight and 2.5% by weight into an absorbent core material containing wood pulp fluff and a superabsorbent polymer. Control materials containing a) wood pulp fluff only, and b) fluff and superabsorbent only, were also prepared. All of the samples were tested for bacteriostatic activity using Standard Test AATCC-100, of the American Association of Textile Chemists and Colorists. This test method is incorporated by reference.

Briefly, a culture medium (Tryptic Soy Agar) was inoculated with the microorganism and 1 mL of the inoculum was then applied to a 2" by 2" piece of the fabric. The neutralizer solution was Letheen Broth. The microorganism population (colony forming units (cfu) per mL) was determined at initial contact time and after a 4-hour contact time at 35–39C.

The following Table 2 summarizes the antimicrobial data for each sample, for three types of odor-forming bacteria.

TABLE 2

Antimicrobial Data

| Example | Composition | Bacteria | Initial Contact | After 4 Hours |
|---|---|---|---|---|
| 9 | 600 gsm fluff | S. aureus | $1.3 \times 10^7$ | $8.5 \times 10^6$ |
| | | | $8.2 \times 10^6$ | $1.7 \times 10^6$ |
| | | E. coli | $3.6 \times 10^7$ | $2.8 \times 10^7$ |
| | | | $3.3 \times 10^7$ | $2.4 \times 10^7$ |
| | | P. mirabilis | $2.0 \times 10^6$ | $1.4 \times 10^4$ |
| | | | $1.6 \times 10^6$ | $6.7 \times 10^3$ |
| 10 | 100 gsm SAP + 500 gsm fluff | S. aureus | $9.3 \times 10^6$ | $6.5 \times 10^6$ |
| | | | $8.7 \times 10^6$ | $7.7 \times 10^6$ |
| | | E. coli | $2.2 \times 10^7$ | $2.9 \times 10^7$ |
| | | | $4.6 \times 10^7$ | $1.5 \times 10^7$ |
| | | P. mirabilis | $1.7 \times 10^6$ | $2.9 \times 10^4$ |
| | | | $1.5 \times 10^6$ | $1.6 \times 10^5$ |
| 11 | 6 gsm Poly-1-Cl + 100 gsm SAP + 494 gsm fluff (1% Poly-1-Cl) | S. aureus | $5.5 \times 10^6$ | $7.5 \times 10^2$ |
| | | | $1.0 \times 10^7$ | $8.9 \times 10^4$ |
| | | E. coli | $3.2 \times 10^7$ | $1.6 \times 10^6$ |
| | | | $3.8 \times 10^7$ | $2.3 \times 10^5$ |
| | | P. mirabilis | $1.0 \times 10^6$ | $<1.0 \times 10^1$ |
| | | | $1.0 \times 10^6$ | $<1.0 \times 10^1$ |
| 12 | 15 gsm Poly-1-Cl + 100 gsm SAP + 485 gsm fluff (2.5% Poly-1-Cl) | S. aureus | $9.0 \times 10^6$ | $<1.0 \times 10^1$ |
| | | | $8.8 \times 10^6$ | $5.5 \times 10^1$ |
| | | E. coli | $3.8 \times 10^7$ | $<1.0 \times 10^1$ |
| | | | $2.4 \times 10^7$ | $<1.0 \times 10^1$ |
| | | P. mirabilis | $2.8 \times 10^5$ | $<1.0 \times 10^1$ |
| | | | $5.9 \times 10^5$ | $<1.0 \times 10^1$ |

For the above examples, the fluff-based composites were produced on a continuous airform line. Particles (SAP, SAP+ Poly-1-Cl) were delivered by a Christy feeder to the forming chamber where mixing with the fluff occurred, followed by web formation on the wire.

The fluff in the composites was CR1654, from U.S. Alliance in Childersberg, Ala. The composites with superabsorbent (SAP) were made with Dow 2035M SAP. The selectively chlorinated Poly-1-Cl was supplied by Halo-Source Corporation.

Duplicate samples from each code were given unique labels. One of the samples from each code was labeled with a number and the other sample was labeled with a letter. The tester challenged pieces (2" by 2") from each letter-labeled sample with the 3 microbes (one microbe per piece) on the same day and all number-labeled samples on a different day. Therefore, each of the two readings shown in the table for the three microbes represents a separate experiment. AATCC Method 100, modified for use of these 3 specified microbes, was used.

The following information is evident from this table:

1. Fluff alone does not affect S. aureus of E. coli. It appears to slightly reduce the P. mirabilis population.

2. Fluff+SAP is not any different than fluff alone.

3. 1% Poly-1-Cl in the presence of SAP and fluff is effective for P. mirabilis and moderately effective for S. aureus. It may be only slightly effective for E. coli.

4. 2.5% Poly-1-Cl in the presence of SAP and fluff is very effective for all 3 microbes.

While the embodiments of the invention disclosed herein are presently preferred, various modifications and improvements can be made without departing from the spirit and scope of the invention. The scope of the invention is indicated by the appended claims, and all changes that fall within the meaning and range of equivalents are intended to be embraced therein.

I claim:

1. An antimicrobial nonwoven web having odor control properties, comprising:

a plurality of nonwoven fibers; and about 0.1–10% by weight of a halogenated polystyrene hydantoin including a plurality of repeating units and halogen atoms chemically linked to the repeating units;

each of the repeating units including an amide nitrogen atom and an imide nitrogen atom;

wherein at least about 90% of the halogen atoms are chemically linked to the amide nitrogen atoms and about 75–100% of the amide nitrogen atoms are chemically linked to halogen atoms.

2. The antimicrobial nonwoven web of claim 1, wherein at least about 95% of the halogen atoms are chemically linked to the amide nitrogen atoms.

3. The antimicrobial nonwoven web of claim 1, wherein at least about 99% of the halogen atoms are chemically linked to the amide nitrogen atoms.

4. The antimicrobial nonwoven web of claim 1, wherein about 100% of the halogen atoms are chemically linked to the amide nitrogen atoms.

5. The antimicrobial nonwoven web of claim 1, wherein the nonwoven fibers comprise absorbent fibers.

6. The antimicrobial nonwoven web of claim 1, further comprising a superabsorbent material.

7. The antimicrobial nonwoven web of claim 1, wherein the nonwoven web comprises nonabsorbent fibers.

8. A personal care absorbent article comprising the antimicrobial nonwoven web of claim 1.

9. A medical absorbent article comprising the antimicrobial nonwoven web of claim 1.

10. An antimicrobial absorbent nonwoven web having odor control properties, comprising:

a plurality of absorbent nonwoven fibers; and about 0.1–10% by weight of a chlorinated polystyrene hydantoin including a plurality of repeating units and chlorine atoms chemically linked to the repeating units;

each of the repeating units including an amide nitrogen atom and an imide nitrogen atom;

wherein at least about 90% of the chlorine atoms are chemically linked to the amide nitrogen atoms.

11. The antimicrobial absorbent nonwoven web of claim 10, comprising about 0.5–5% by weight of the chlorinated polystyrene hydantoin.

12. The antimicrobial absorbent nonwoven web of claim 10, comprising about 1–3% by weight of the chlorinated polystyrene hydantoin.

13. The antimicrobial absorbent nonwoven web of claim 10, wherein at least about 95% of the chlorine atoms are chemically linked to the amide nitrogen atoms.

14. The antimicrobial absorbent nonwoven web of claim 10, wherein at least about 99% of the chlorine atoms are chemically linked to the amide nitrogen atoms.

15. The antimicrobial absorbent nonwoven web of claim 10, wherein about 100% of the chlorine atoms are chemically linked to the amide nitrogen atoms.

16. The antimicrobial absorbent nonwoven web of claim 10, wherein the absorbent nonwoven fibers comprise cellulose fibers.

17. The absorbent antimicrobial nonwoven web of claim 10, further comprising a superabsorbent material.

18. A personal care absorbent article comprising the antimicrobial absorbent nonwoven web of claim 10.

19. A medical absorbent article comprising the antimicrobial absorbent nonwoven web of claim 10.

20. An antimicrobial non-retentive nonwoven web having odor control properties, comprising:
a plurality of non-retentive nonwoven fibers; and
about 0.1–10% by weight of a chlorinated polystyrene hydantoin including a plurality of repeating units and chlorine atoms chemically linked to the repeating units;
each of the repeating units including an amide nitrogen atom and an imide nitrogen atom;
wherein at least about 90% of the chlorine atoms are chemically linked to the amide nitrogen atoms.

21. The antimicrobial non-retentive nonwoven web of claim 20, comprising about 0.5–5% by weight of the chlorinated polystyrene hydantoin.

22. The antimicrobial non-retentive nonwoven web of claim 20, comprising about 1–3% by weight of the chlorinated polystyrene hydantoin.

23. The antimicrobial non-retentive nonwoven web of claim 20, wherein the nonwoven fibers comprise spunbond fibers.

24. The antimicrobial non-retentive nonwoven web of claim 20, wherein the nonwoven fibers comprise meltblown fibers.

25. The antimicrobial non-retentive nonwoven web of claim 20, wherein the nonwoven fibers comprise bonded carded fibers.

26. The antimicrobial non-retentive nonwoven web of claim 20, wherein the nonwoven fibers comprise air laid fibers.

27. A personal care absorbent article comprising the antimicrobial non-retentive nonwoven web of claim 20.

28. A medical absorbent article comprising the antimicrobial non-retentive nonwoven web of claim 20.

29. An industrial wipe comprising the antimicrobial nonwoven web of claim 1.

30. A food wipe comprising the antimicrobial nonwoven web of claim 1.

31. An industrial wipe comprising the antimicrobial absorbent nonwoven web of claim 10.

32. A food wipe comprising the antimicrobial absorbent nonwoven web of claim 10.

33. An industrial wipe comprising the antimicrobial non-retentive nonwoven web of claim 20.

34. A food wipe comprising the antimicrobial non-retentive nonwoven web of claim 20.

* * * * *